US012626825B2

(12) United States Patent
Miranda et al.

(10) Patent No.: US 12,626,825 B2
(45) Date of Patent: *May 12, 2026

(54) PHONE CALL TO PATIENT FROM WITHIN VIDEO CALL

(71) Applicant: Doximity, Inc., San Francisco, CA (US)

(72) Inventors: Bruno Paladini Miranda, San Diego, CA (US); Jey Balachandran, San Francisco, CA (US); Rob Malko, Atlanta, GA (US); Jeremiah Konoske, Davis, CA (US); Joel Davis, San Francisco, CA (US)

(73) Assignee: Doximity, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/536,993

(22) Filed: Dec. 12, 2023

(65) Prior Publication Data

US 2024/0112821 A1 Apr. 4, 2024

Related U.S. Application Data

(63) Continuation of application No. 17/714,054, filed on Apr. 5, 2022, now Pat. No. 11,929,181.

(60) Provisional application No. 63/173,188, filed on Apr. 9, 2021.

(51) Int. Cl.
G16H 80/00 (2018.01)
H04L 12/18 (2006.01)

(52) U.S. Cl.
CPC ......... G16H 80/00 (2018.01); H04L 12/1818 (2013.01); H04L 12/1822 (2013.01)

(58) Field of Classification Search
None
See application file for complete search history.

(56) References Cited

U.S. PATENT DOCUMENTS

| 11,043,293 | B1 * | 6/2021 | Salzbrenner | ........... | G16H 10/60 |
| 2011/0119290 | A1 * | 5/2011 | Dhoble | ................. | G16H 80/00 |
| | | | | | 707/769 |

(Continued)

FOREIGN PATENT DOCUMENTS

CN 110708497 B 2/2021

OTHER PUBLICATIONS

International Search Report and the Written Opinion of the International Searching Authority for PCT Application No. PCT/US2022/023683 mailed Jul. 8, 2022.

(Continued)

*Primary Examiner* — Phyllis A Book
(74) *Attorney, Agent, or Firm* — Womble Bond Dickinson (US) LLP

(57) ABSTRACT

A system and method are described that includes initiating an online video call between a healthcare provider device and a patient device. The method also includes receiving a request to place a phone call, separate from the online video call, from the healthcare provider device to the patient device from within the online video call. The method further includes initiating the phone call between the healthcare provider device and the patient device from within the online video call without disconnecting the healthcare provider device from the online video call.

20 Claims, 7 Drawing Sheets

(56) References Cited

U.S. PATENT DOCUMENTS

| | | | | |
|---|---|---|---|---|
| 2011/0184763 A1* | 7/2011 | Schoenberg | .......... | G16H 10/20 |
| | | | | 705/3 |
| 2013/0060576 A1* | 3/2013 | Hamm | ................... | G16H 40/67 |
| | | | | 705/2 |
| 2013/0096937 A1 | 4/2013 | Campbell et al. | | |
| 2013/0317843 A1* | 11/2013 | Schoenberg | .......... | G16Z 99/00 |
| | | | | 705/2 |
| 2014/0050307 A1 | 2/2014 | Yuzefovich | | |
| 2014/0257851 A1 | 9/2014 | Walker et al. | | |
| 2015/0081629 A1* | 3/2015 | Newman | ............ | H04L 67/1095 |
| | | | | 707/613 |
| 2015/0215753 A1* | 7/2015 | Leipzig | ................... | H04W 8/22 |
| | | | | 455/419 |
| 2015/0227944 A1* | 8/2015 | Comey | ............... | G06Q 30/018 |
| | | | | 705/3 |
| 2015/0278453 A1* | 10/2015 | Joao | ....................... | G16H 80/00 |
| | | | | 705/3 |
| 2016/0188799 A1* | 6/2016 | Borras | ..................... | H04N 7/15 |
| | | | | 434/428 |
| 2017/0004273 A1* | 1/2017 | Mbanefo | ............... | G16H 80/00 |
| 2017/0011192 A1* | 1/2017 | Arshad | ................. | G16H 40/20 |
| 2017/0116384 A1* | 4/2017 | Ghani | .................... | G16H 70/20 |
| 2017/0155630 A1* | 6/2017 | East | ........................ | H04L 63/08 |
| 2018/0121857 A1* | 5/2018 | Gutman | ................ | G16H 15/00 |
| 2018/0268106 A1* | 9/2018 | Velaga | ................ | G06F 16/2428 |
| 2019/0096534 A1 | 3/2019 | Joao | | |
| 2020/0058410 A1 | 2/2020 | Khouri et al. | | |
| 2020/0066414 A1* | 2/2020 | Neff | .................... | H04L 12/1818 |
| 2020/0075147 A1* | 3/2020 | Farhat | ................. | G06Q 20/102 |
| 2020/0251226 A1* | 8/2020 | Vo | .......................... | G16H 40/20 |
| 2020/0365244 A1 | 11/2020 | Shah et al. | | |
| 2021/0005326 A1* | 1/2021 | Soza | ..................... | G16H 20/00 |
| 2021/0183505 A1 | 6/2021 | Velaga | | |
| 2021/0280323 A1* | 9/2021 | Soza | ..................... | G16H 40/67 |
| 2021/0304902 A1* | 9/2021 | Rosen | ................... | G16H 80/00 |
| 2021/0319895 A1 | 10/2021 | Joao | | |
| 2022/0189625 A1* | 6/2022 | Pomianowski | ........ | G16H 40/20 |

OTHER PUBLICATIONS

International Preliminary Report on Patentability from related PCT Application No. PCT/US2022/023683 mailed Oct. 19, 2023, 11 pages.

* cited by examiner

200

151 Healthcare Provider

205 Open Application

Authentication Passed

210 Initiate Video Call

Send Provider into Call

110 Authentication Server

Call Room 212

Send Phone Number

Return Video Call Details

130 Video Server

Send Patient into Call

Validate Clicked Link

Send Link

120 Messaging Server

141 Patient

Send Message to Patient

300

302

Initiate an online video call between a
healthcare provider device and a patient
device

304

Receive a request to place a phone call from
the healthcare provider device to the patient
device from within the video call

306

Initiate a phone call between the healthcare
provider device and the patient device from
within the video call

550

PHONE CALL TO PATIENT FROM WITHIN VIDEO CALL

RELATED APPLICATIONS

This application claims priority from U.S. patent application Ser. No. 17/714,054, filed on Apr. 5, 2022, which claims priority from and the benefit of U.S. Provisional Patent Application No. 63/173,188 filed on Apr. 9, 2021, the entire contents of which are incorporated herein by reference in their entirety.

TECHNICAL FIELD

This disclosure generally relates to video calls. In particular, this disclosure relates to initiating a phone call to a user from within a video call.

BACKGROUND

Healthcare providers (e.g., doctors, nurses, etc.) may provide various health related services and products to patients. Patients may often visit health care facilities (e.g., hospitals, clinics, etc.) to receive the health related services and products. For example, a patient may visit a clinic or a hospital for a checkup or to speak with a doctor about a particular medical/health issue.

BRIEF DESCRIPTION OF THE DRAWINGS

Embodiments and implementations of the present disclosure will be understood more fully from the detailed description given below and from the accompanying drawings of various aspects and implementations of the disclosure, which, however, should not be taken to limit the disclosure to the specific embodiments or implementations, but are for explanation and understanding only.

DETAILED DESCRIPTION

As discussed above, patients often visit healthcare professionals at physical locations to receive health related services and/or products. As healthcare continues to evolve, more efficient and/or convenient methods of providing health related services and/or products may be used. For example, rather than visiting a healthcare professional in person, it may be more convenient to have a video call (e.g., a video conference) between a healthcare professional and a user. However, a user may not be proficient in the use of computing devices and/or applications for joining or setting up video calls. For example, some patients may have more difficulty typing in an identifier for a video call and a password for the video call. Thus, an easier and/or more efficient method of joining or setting up a video call between a patient and a healthcare professional may be useful. Additionally, patients may not be able to immediately join a video call and may need reminders, or help, to join the call. Thus, a method of allowing a healthcare professional to initiate a video call and provide reminders, such as placing a call to the patient from within the video call, to help or remind the patient to join the video call while waiting for the patient to join the call may also be useful.

Figure 1:
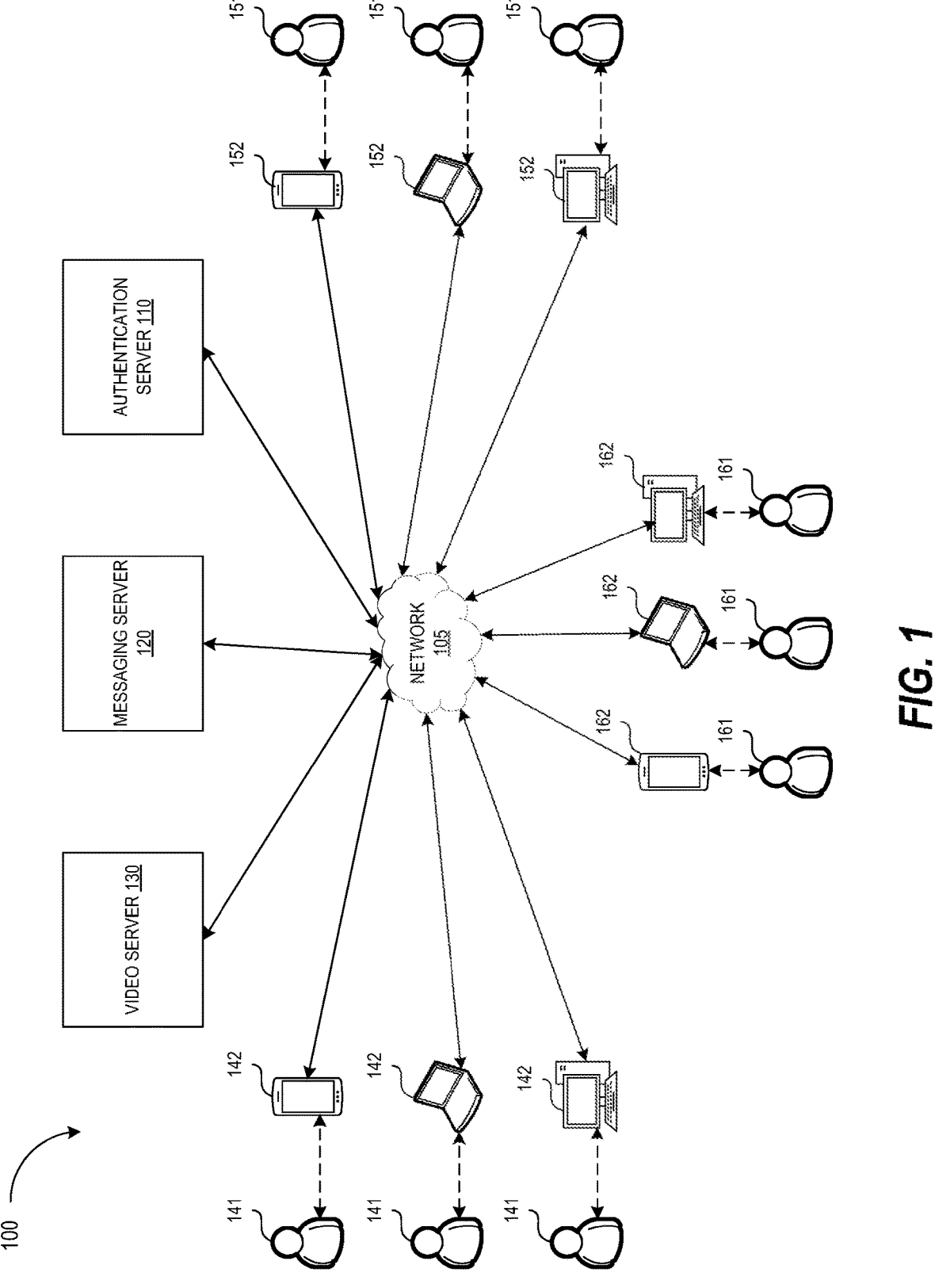
FIG. 1 is a diagram illustrating an example network architecture in accordance with one or more embodiments of the disclosure.

FIG. 1 is a diagram illustrating an example network architecture 100, in accordance with one or more embodiments of the disclosure. The network architecture 100 includes network 105, an authentication server 110, a messaging server 120, a video server 130, users 141, computing devices 142, healthcare providers 151, computing devices 152, service providers 161, and computing devices 162.

In one embodiment, the users 141 may be patients who use services and/or products provided by one or more of the healthcare providers 151 and service providers 161. Each user 141 may use a computing device 142 to communicate with one or more of a healthcare provider 151 and a service provider 161. Examples of computing devices 142 may include, but are not limited to, a smartphone, a tablet computer, a laptop computer, a desktop computer, etc.

In one embodiment, the healthcare providers 151 may be people who provide health related services and/or products to the user. Examples of healthcare providers 151 may include, but are not limited to, doctors, pharmacists, dentists, nurses, therapists, psychologists, technicians, surgeons, etc. Each healthcare provider 151 may use a computing device 152 (e.g., smartphone, tablet computer, etc.) to communicate with one or more of the users 141 and the service providers 161.

In one embodiment, a service provider 161 may provide additional or ancillary services to one or more of the users 141 and the healthcare providers 151. Examples of service providers 151 may include, but are not limited to, insurance providers, translators (e.g., language translators), billing specialists, etc. Each service provider 161 may use a computing device 162 (e.g., smartphone, tablet computer, etc.) to communicate with one or more of the users 141 and the healthcare providers 151.

As discussed above, a healthcare provider 151 (e.g., a doctor) may communicate with a user (e.g., a patient) via a video call (e.g., a video conference, a video meeting, etc.). The system architecture 100 may allow a healthcare provider 151 to provide a user 151 with a link that allows the user 151 to join or setup a video call with the healthcare provider 151. In one embodiment, the user 151 may be able to join or setup the video call without providing or using security credentials, such as a password, and/or without providing a meeting identifier.

In one embodiment, the authentication server 110 may authenticate one or more of the healthcare provider 151, a service provider 161, and a user 141. For example, a computing device 152 (used by the healthcare provider 151) may include an app (e.g., an application, a program, etc.) that allows the healthcare provider 151 to join or setup the video call with the user 141. The app may prompt the healthcare provider 151 for a user name, password, or other security credentials before allowing the user to join or setup the video call. The app may provide the security credentials to the authentication server 110 which may authenticate or verify the security credentials. After the security credentials of the healthcare provider 151 have been verified, the healthcare provider 151 may be allowed to setup or join the video call.

In one embodiment, the messaging server 120 may send or transmit the link to a computing device 142 of the user 141. For example, the healthcare provider 141 may setup a video call with the user via the app on the computing device 152. The app may communicate with the video server 130 and the video server 130 may communicate with the messaging server 120 to indicate that the healthcare provider 141 wants to setup a video call with the user 141. The video server 130 may generate a video call (e.g., a room, chat, etc.) on the video server 130. The messaging server 120 may transmit or send the link for the video call to the computing device 142 of the user. For example, the messaging server 120 may send a short message service (SMS) message to the computing device 142 of the user 141.

In one embodiment, the video server 130 may host the video call between the healthcare provider 151 and the user 141. For example, after the user selects, clicks, activates, etc., the link, the computing device 142 may communicate with the video server 130 to setup or join the video call. The video call may forward data (e.g., video data, video frames, audio data, audio frames, etc.) between the computing device 142 (of the user 141) and the computing device 152 (of the user 151). The video server 130 may also allow different people to join or leave a video call. For example, a first healthcare provider 151 may initiate the video call with the user 141. At a later point in time, the first healthcare provider 151 may add a second healthcare provider 151 to the video call and the first healthcare provider 151 may leave the video call. The video server 130 may forward data between the computing devices of the people who are added or removed from the video call.

In one embodiment, the link may allow the user 141 to join or setup the video call without providing or using security credentials, such as a password. For example, by selecting, clicking, activating, etc., the link, the computing device 142 of the user 141 may automatically setup or join a video call with the healthcare provider 151. The user 141 may not be prompted for security credentials to join or setup the video call. For example, the link may include credentials and/or other information necessary to securely join the video call.

In one embodiment, the link may include various portions or pieces of data. For example, the link may include one or more of a location of a server (e.g., the video server 130), one or more identifiers, a time period, and a signature. The link may allow the user 141 to join the video call without providing security credentials (e.g., without entering a password) and/or without providing an identifier for the meeting (e.g., a meeting ID, a meeting name, etc.). This may allow the user 141 to join the video call more quickly and/or easily. The different portions of pieces of data link in the link are discussed in more detail below. Although some examples and embodiments are described herein with respect to a healthcare provider, a service provider, or a user (e.g., a patient) it should be noted that embodiments may be used in any context in which a video call is initiated for others to join. Furthermore, any actions described herein as being performed by a healthcare provider, a service provider, or a user may be performed by a computing device of the healthcare provider, service provider, or user.

Figure 2:
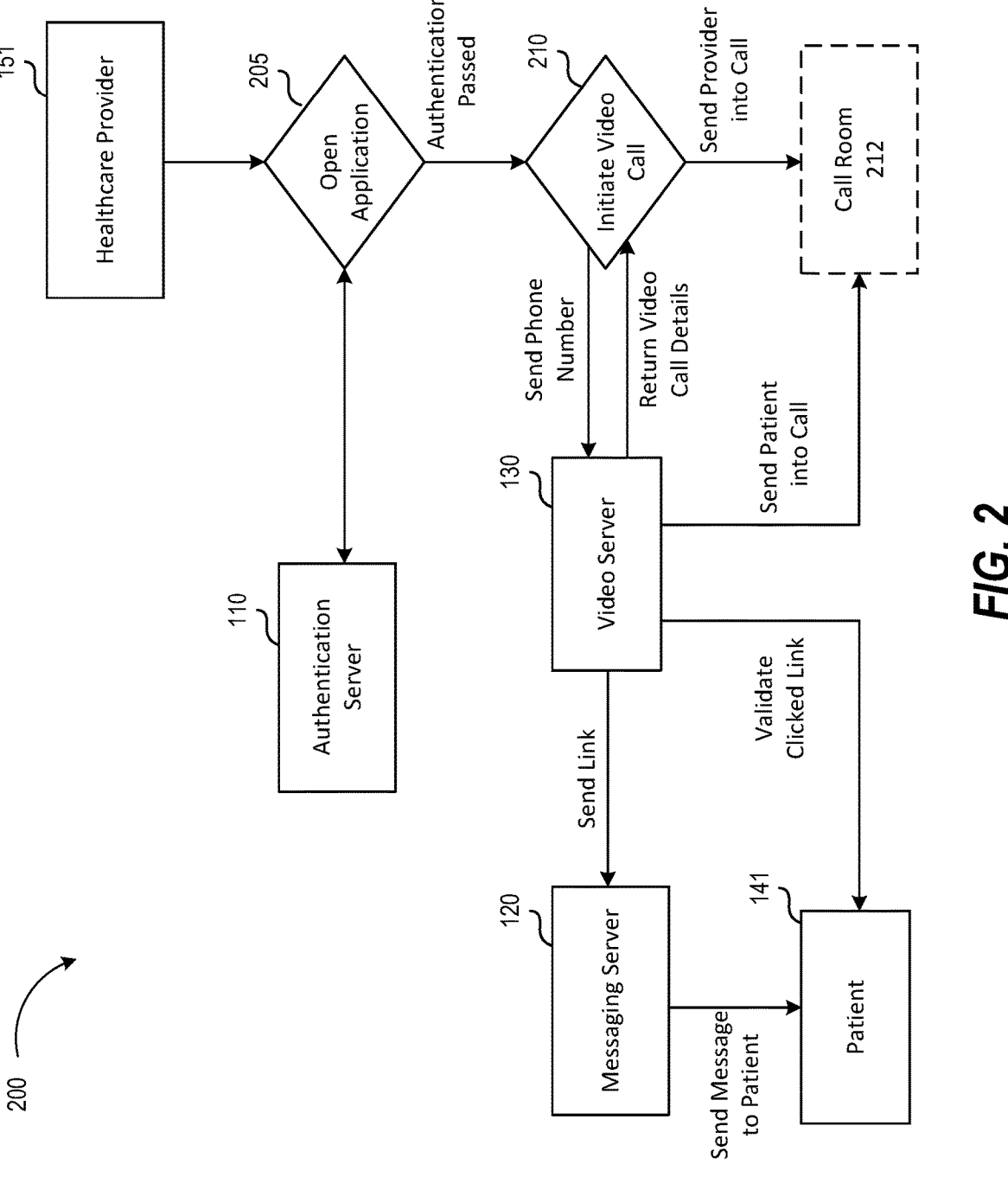
FIG. 2 is a flow diagram of an example process of setting up a video call in accordance with one or more embodiments of the disclosure.

FIG. 2 is a flow diagram of a process 200 of setting up a video call in accordance with one or more embodiments of the present disclosure. Process 200 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the process 200 may be performed by various computing devices, such as an authentication server, a messaging server, a video server, etc. The actions of the user 141 may be performed by a computing device of the user 141 (e.g., computing device 142 illustrated in FIG. 1) and the actions of the healthcare provider 151 may be performed by a computing device of the healthcare provider 151 (e.g., computing device 152 illustrated in FIG. 1).

The process 200 begins at block 205, wherein a healthcare provider 151 (e.g., a doctor) may use, open, etc., an app (e.g., an application, software, etc.) to setup or initiate a video call with the user 141 (e.g., a patient). The user may be prompted for security credentials which may be provided to the authentication server 110 for verification or authentication. If the security credentials are verified, at block 210 the application may initiate a video call and may communicate with the video server 130 to setup the video call, which the user may join at a later time. The healthcare provider 151 may also provide a phone number, email address, name, etc., of the user 141 so that the messaging server 120 is able to determine which user to send the message and/or link to.

The video server 130 may also communicate with the messaging server 120 to indicate that the healthcare professional 151 wants to setup a video call with the user 141. The messaging server 120 may transmit message (e.g., an SMS message, a MMS message, a chat message, a text message, etc.) to the user 141 to indicate that the healthcare professional 151 wants to setup a video call with the user 141. The message may include a link that allows the user 141 to join the video call. The link may allow the user 141 to join the video call without providing security credentials (e.g., without entering a password). This may allow the user 141 to join the video call more quickly and/or easily. The link is discussed in more detail below.

When the user 141 activates, clicks, selects, etc., the link, the user may automatically join the video call initiated by the healthcare professional 151. The user 141 may be connected to the video server 130 so that the video server 130 can allow the user 141 to join the video call with the healthcare provider 151. For example, the video server 130 may place the healthcare provider 151 and the user 141 in a room 212 (e.g., a call room, a video meeting room, a virtual room, etc.).

In one example, after initiating the video call the healthcare professional 151 can stay on the video call and wait for the user 141 to join the video call. Alternatively, the healthcare professional 151 can leave the call while waiting and the video server 130 may provide a notification to the healthcare professional 151 when the user 141 joins the video call. In one example, the computing device 152 may provide, via the app, an option for the healthcare professional 151 to place a phone call to the computing device 142 of the user 141 to nudge the user to join the call and/or help the user join the call. In another example, the app may provide the healthcare professional 151 options to provide other forms of reminders to the computing device 142 of the user 141 (e.g., additional text message, email, etc.) for the user 141 to join the video call.

Figure 3:
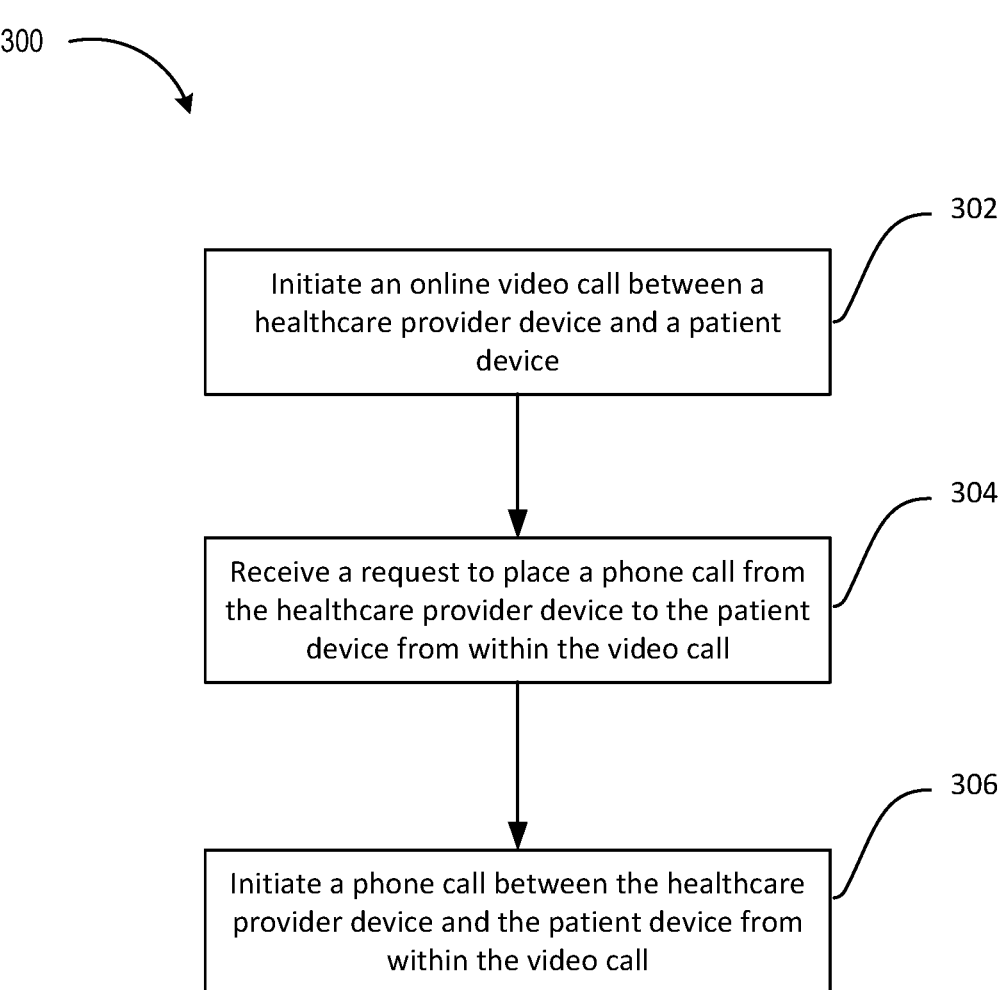
FIG. 3 is a flow diagram of an example process of initiating a phone call from within the video call in accordance with one or more embodiments of the disclosure.

FIG. 3 is a flow diagram of a process 300 of providing a phone call from within a video call in accordance with one or more embodiments of the present disclosure. Process 300 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the process 300 may be performed by various computing devices, such as an authentication server, a messaging server, a video server, etc. The actions of the user 141 may be performed by a computing device of the user 141 (e.g., computing device 142 illustrated in FIG. 1) and the actions of the healthcare provider 151 may be performed by a computing device of the healthcare provider 151 (e.g., computing device 152 illustrated in FIG. 1).

Process 300 begins at block 302, where processing logic initiates an online video call between a healthcare provider device and a patient device. For example, the healthcare provider may set up the video call with the patient including video call details, authentication credentials, patient phone number, time of the video call, etc. The processing logic may generate the online video call (e.g., at a video server such as video server 130 of FIG. 1) and create a link to access the video call. The processing logic may provide the link to the user via a message, such as a text message, email, chat message, etc. The link may include credentials for the video call so that the user/patient can access the video call by selecting the link and without requiring any credentials or details of the video call.

At block 304, the processing logic receives a request to place a phone call from the healthcare provider device to the patient device from within the online video call. For example, the patient may not join the video call right away or may not join the video call at the scheduled time. Accordingly, the healthcare provider may have to wait for the patient to join the video call. In some examples, the processing logic may provide an option, from within the video call, for the healthcare provider to place a phone call to the patient. For example, the interface of the video call displayed to the healthcare provider may include an icon for placing a call directly to the patient from within the video call.

At block 306, the processing logic initiates a phone call between the healthcare provider device and the patient device from within the video call. Upon receiving the request to place the phone call from within the video call, the processing logic may place the call while the video call remains online. For example, the healthcare provider device may place the video call connection in the background to make the phone call to the patient device. The video call may continue to execute on the video server and once the call ends, the healthcare provider device may return the video call connection to the operational foreground. Accordingly, the healthcare provider can seamlessly initiate the video call, place a phone call to the patient to help the patient join the video call, and then return to the video call (e.g., once the patient has joined).

Figure 4:
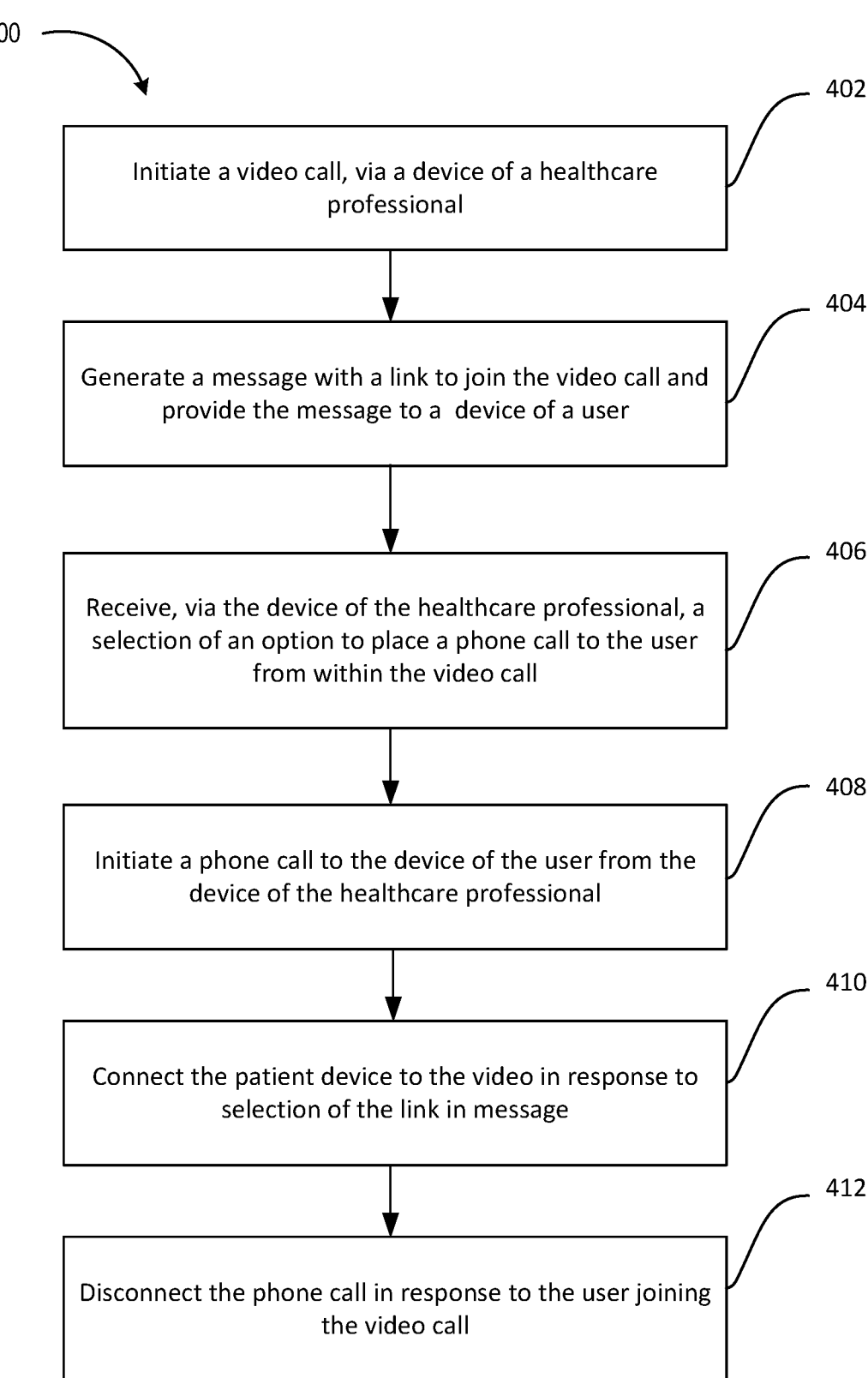
FIG. 4 is a flow diagram of an example process of initiating a phone call reminder to join a video call from within the video call in accordance with one or more embodiments of the disclosure.

FIG. 4 is a flow diagram of a process 400 of providing a phone call, or other reminder, to a video call in accordance with one or more embodiments of the present disclosure. Process 400 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the process 400 may be performed by various computing devices, such as an authentication server, a messaging server, a video server, etc. The actions of the user 141 may be performed by a computing device of the user 141 (e.g., computing device 142 illustrated in FIG. 1) and the actions of the healthcare provider 151 may be performed by a computing device of the healthcare provider 151 (e.g., computing device 152 illustrated in FIG. 1).

The process 400 begins at block 402, where a healthcare provider initiates a video call. The healthcare provider may initiate the video call via a video call application on a device of the healthcare provider.

At block 404, a video call server generates a message with a link to join the video call and provides the message to a user (e.g., a patient). In some examples, a messaging service may provide the message to the user with the link. For example, a text messaging service, an email service, an online chat service, etc. may send the message to the user including the link to the video call. As described above, the message may be a text message, or any other message type. Additionally, the link included in the message may allow the user to join the video call without entering a password or any other credentials for the video call. In one example, the healthcare professional may hang up the video call and may be provided with a notification (e.g., from the video server 130) when the patient has joined the call.

At block 406, the healthcare professional may select an option to place a phone call to the user from within the video call (e.g., via user interface 505 described below in FIG. 5A). For example, after creation of the video call and before the patient joins the call, the device of the healthcare professional may display an icon within the video call (e.g., within the video call application) for placing a phone call to the patient device. Accordingly, the healthcare professional may select the icon to make the call to the patient within the video call (e.g., without exiting the video call application).

At block 408, the device used by the healthcare profession may initiate the phone call to the user (e.g., via the video call application). The video call may continue to run in the background of the device used by the healthcare professional during the phone call to the patient. For example, the phone call may be made from within the video call application on the healthcare provider device. In some examples, during the phone call the device of the healthcare professional may also display instructions for helping the patient join the video, as depicted in FIG. 5B.

At block 410, the processing logic connects the patient device to the video call in response to patient selection of the link in the message. In some examples, the link may include a location of the video call, a time, access credentials, etc. to allow the patient to join the video call without providing credentials. For example, selection of the link may direct the patient device directly into the video call with no additional actions required on behalf of the patient.

At block 412, the device may disconnect the phone call in response to the user joining the video call (e.g., via the link provided in the text message described above). Once the patient/user has joined the video call, the device of the healthcare provider may return the interface to the video call. In some examples, upon determining that the patient has joined the video call (e.g., via notification, etc.) the healthcare provider device may automatically disconnect the phone call and return to the video call.

Figure 5A:
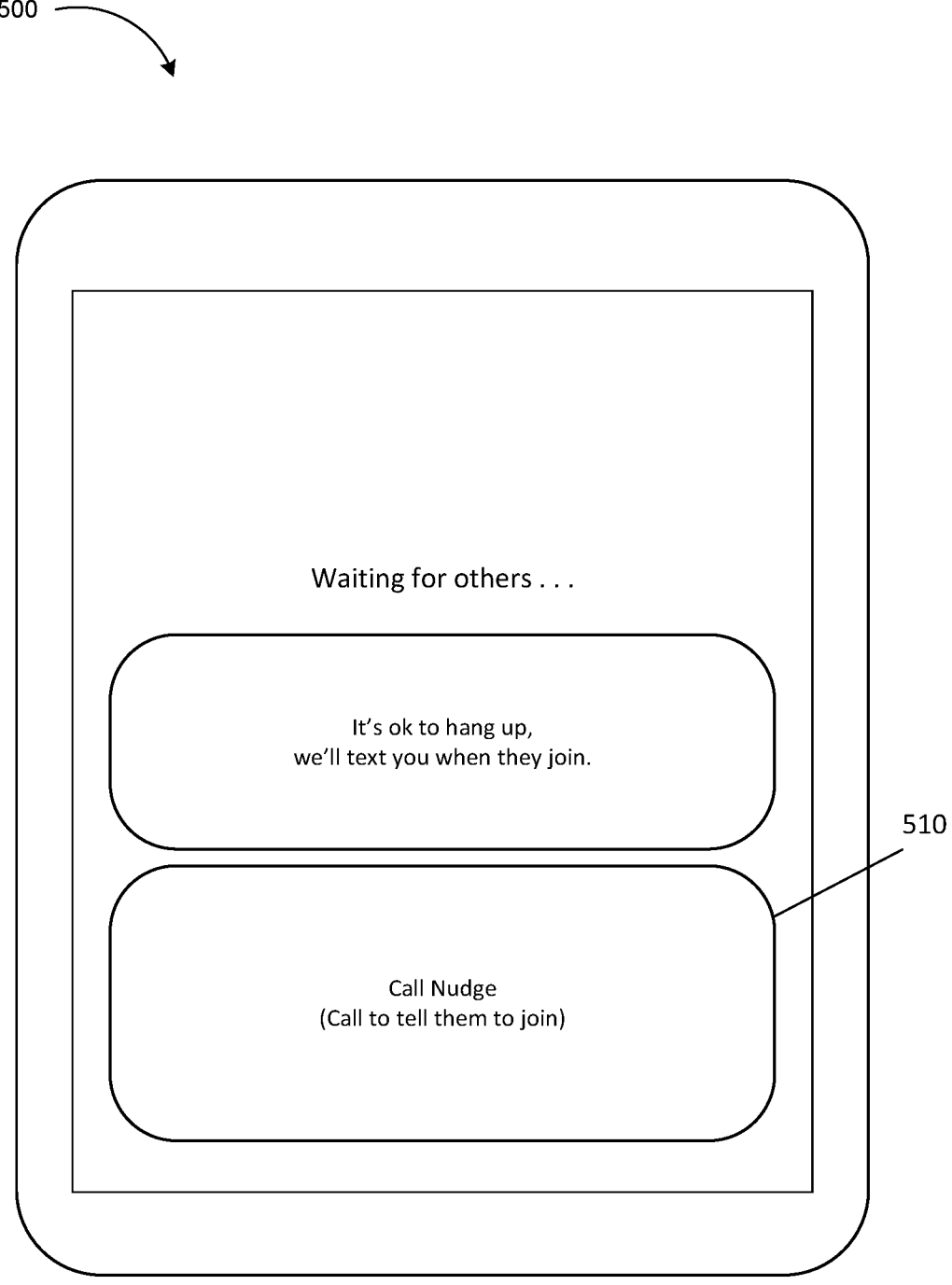
FIG. 5A is diagram illustrating an example user interface in accordance with one or more embodiments of the disclosure.
Figure 5B:
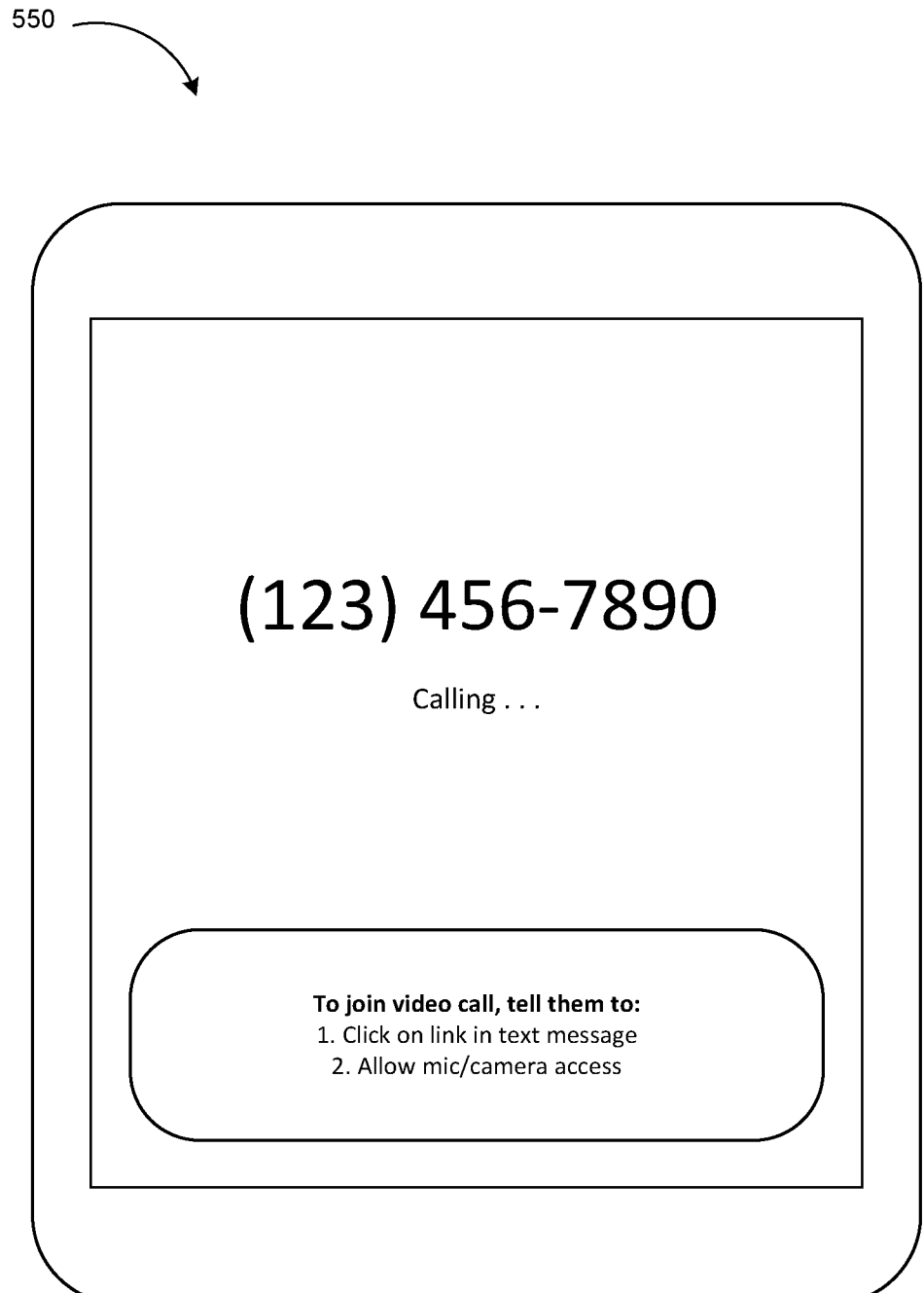
FIG. 5B is diagram illustrating an example user interface in accordance with one or more embodiments of the disclosure.

FIG. 5A illustrates a diagram of a user interface 500 according to some embodiments. The user interface 500 may be displayed by a user device executing a video call application, as described above. The user interface 500 may be displayed after a healthcare professional has initiated a video call with a patient but before the patient has joined the video call. As depicted, the user interface 500 may display one or more messages. For example, the user interface 500 may indicate to the healthcare professional that they can hang up the call and that they will be notified (e.g., via text message, or other notification) when the user (e.g., patient) has joined the call. Additionally, the user interface 500 may display an option 510 for the healthcare professional to place a phone call to the patient from within the video call (i.e., without hanging up the video call). Upon selection of option 510, the user device may place a phone call to the patient device from within the video call application. The video call may be placed in the background during the phone call. After the patient joins the video call, or after the phone call is terminated, the user device may return to the interface 500 for the video call with the patient.

FIG. 5B illustrates a diagram of a user interface 550 according to some embodiments. The user interface 500 may be displayed by a user device executing a video call application, as described above. The user interface 550 may be displayed in response to the healthcare provider selecting the "call nudge" option provided by user interface 500 of FIG. 5A. As depicted, the phone call may be initiated and connected from within the video call application. The user interface 550 may further provide an informational message to the healthcare provider with instructions for how the patient can join the video call (e.g., to help the healthcare provider instruct the patient via the phone call how to join the video call). For example, the instructions may indicate that to join the call the patient should click on the link in the text message (i.e., text message providing the link to the video call to the patient) and to allow microphone and camera access.

Figure 6:
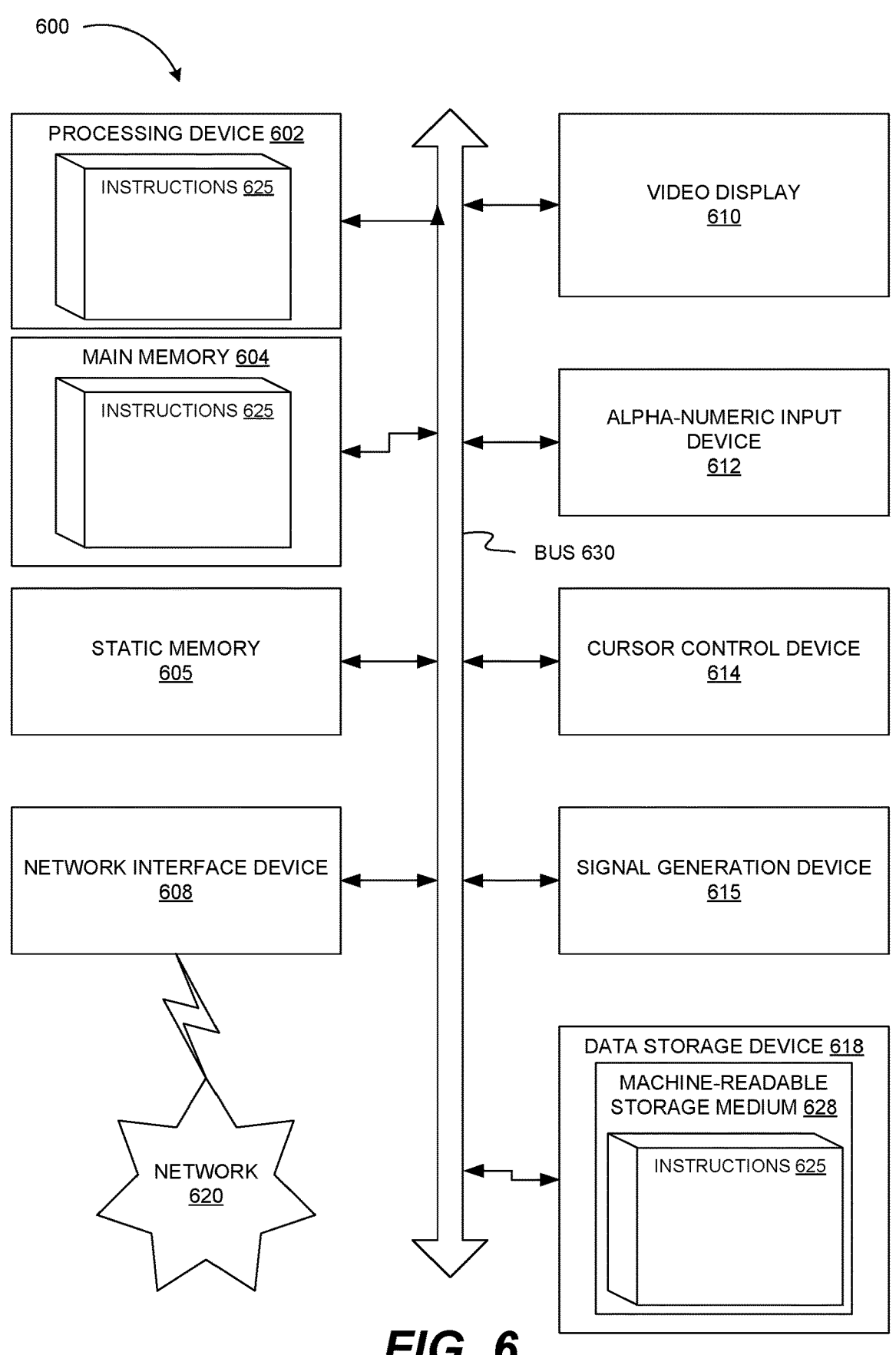
FIG. 6 is a block diagram of an example apparatus that may perform one or more of the operations described herein, in accordance with some embodiments of the present disclosure.

FIG. 6 is a block diagram of an example computing device 600 that may perform one or more of the operations described herein, in accordance with some embodiments. Computing device 600 may be connected to other computing devices in a LAN, an intranet, an extranet, and/or the Internet. The computing device may operate in the capacity of a server machine in the client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 600 may include a processing device (e.g., a general purpose processor, a PLD, etc.) 602, a main memory 604 (e.g., synchronous dynamic random access memory (DRAM), read-only memory (ROM)), a static memory 606 (e.g., flash memory and a data storage device 618), which may communicate with each other via a bus 630.

Processing device 602 may be provided by one or more general-purpose processing devices such as a microprocessor, central processing unit, or the like. In an illustrative example, processing device 602 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 602 may also comprise one or more special-purpose processing devices such as an application specific integrated circuit (ASIC), a field programmable gate array (FPGA), a digital signal processor (DSP), network processor, or the like. The processing device 602 may be configured to execute the operations described herein, in accordance with one or more aspects of the present disclosure, for performing the operations and steps discussed herein.

Computing device 600 may further include a network interface device 608 which may communicate with a network 620. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse) and an acoustic signal generation device 616 (e.g., a speaker). In one embodiment, video display unit 610, alphanumeric input device 612, and cursor control device 614 may be combined into a single component or device (e.g., an LCD touch screen).

Data storage device 618 may include a computer-readable storage medium 628 on which may be stored one or more sets of instructions 625 that may include instructions for carrying out the operations described herein, in accordance with one or more aspects of the present disclosure. Instructions 625 may also reside, completely or at least partially, within main memory 604 and/or within processing device 602 during execution thereof by computing device 600, main memory 604 and processing device 602 also constituting computer-readable media. The instructions 625 may further be transmitted or received over a network 620 via network interface device 608.

While computer-readable storage medium 628 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A method, comprising:

initiating a video call connection for an online video call between a healthcare provider device and a patient device;

receiving, by a processing device, a request to place a phone call, separate from the online video call, from the healthcare provider device to the patient device from within the online video call to nudge the patient device to join the video call when the patient device has not joined the video call;

initiating, by the processing device, a phone call connection for the phone call between the healthcare provider device and the patient device from within the online video call, wherein the phone call connection is initiated on the healthcare provider device during and separately from the video call connection and the online video call continues during the phone call and after the phone call is terminated without disconnecting the healthcare provider device from the video call connection.

2. The method of claim 1, further comprising placing the online video call in a background of the healthcare provider device during the phone call between the healthcare provider device and the patient device.

3. The method of claim 1, further comprising, in response to determining that the patient device has joined the online video call, automatically disconnecting the phone call and returning the healthcare provider device to the online video call.

4. The method of claim 1, further comprising providing, via a user interface of the healthcare provider device, an option to initiate the phone call to the patient device from within the online video call.

5. The method of claim 1, further comprising, in response to initiating the online video call, providing, to the patient device, a message with a link to join the online video call.

6. The method of claim 5, wherein the link allows the patient device to join the online video call without a password or an identifier of the online video call.

7. A system comprising:

a memory; and a processing device, operatively coupled to the memory, to:

initiate a video call connection for an online video call between a healthcare provider device and a patient device;

receive a request to place a phone call, separate from the online video call, from the healthcare provider device to the patient device from within the online video call to nudge the patient device to join the video call when the patient device has not joined the video call;

initiate a phone call connection for the phone call between the healthcare provider device and the patient device from within the online video call, wherein the phone call connection is initiated on the healthcare provider device during and separately from the video call connection and the online video call continues during the phone call and after the phone call is terminated without disconnecting the healthcare provider device from the video call connection.

8. The system of claim 7, wherein the processing device is further to place the online video call in a background of the healthcare provider device during the phone call between the healthcare provider device and the patient device.

9. The system of claim 7, wherein the processing device is further to, in response to determining that the patient device has joined the online video call, automatically disconnect the phone call and returning the healthcare provider device to the online video call.

10. The system of claim 7, wherein the processing device is further to provide, via a user interface of the healthcare provider device, an option to initiate the phone call to the patient device from within the online video call.

11. The system of claim 7, wherein the processing device is further to, in response to initiating the online video call, provide, to the patient device, a message with a link to join the online video call.

12. The system of claim 7, wherein the online video call continues to operate during the phone call.

13. A non-transitory computer readable storage medium including instructions stored therein, that when executed by a processing device, cause the processing device to:

initiate a video call connection for an online video call between a healthcare provider device and a patient device;

receive a request to place a phone call, separate from the online video call, from the healthcare provider device to the patient device from within the online video call to nudge the patient device to join the video call when the patient device has not joined the video call;

initiate, by the processing device, a phone call connection for the phone call between the healthcare provider device and the patient device from within the online video call, wherein the phone call connection is initiated on the healthcare provider device during and separately from the video call connection and the online video call continues during the phone call and after the phone call is terminated without disconnecting the healthcare provider device from the video call connection.

14. The non-transitory computer readable storage medium of claim 13, wherein the processing device is further to place the online video call in a background of the healthcare provider device during the phone call between the healthcare provider device and the patient device.

15. The non-transitory computer readable storage medium of claim 13, wherein the processing device is further to, in response to determining that the patient device has joined the online video call, automatically disconnect the phone call and return the healthcare provider device to the online video call.

16. The non-transitory computer readable storage medium of claim 13, wherein the processing device is further to provide, via a user interface of the healthcare provider device, an option to initiate the phone call to the patient device from within the online video call.

17. The non-transitory computer readable storage medium of claim 13, wherein the processing device is further to in response to initiating the online video call, provide a message to the patient device with a link to join the online video call.

18. The non-transitory computer readable storage medium of claim 17, wherein the link allows the patient device to join the online video call directly from the message.

19. The non-transitory computer readable storage medium of claim 18, wherein the link allows the patient device to join the online video call without a password or an identifier of the online video call.

20. The non-transitory computer readable storage medium of claim 13, wherein the online video call continues to operate during the phone call.

* * * * *